(12) United States Patent  (10) Patent No.: US 9,387,004 B2
Young et al.  (45) Date of Patent: Jul. 12, 2016

(54) ULTRASONIC CUTTING TOOL

(71) Applicant: SRA DEVELOPMENTS LIMITED, South Devon (GB)

(72) Inventors: Michael John Radley Young, South Devon (GB); Stephen Michael Radley Young, South Devon (GB)

(73) Assignee: SRA DEVELOPMENTS LIMITED, South Devon (GB)

( * ) Notice: Subject to any disclaimer, the term of this patent is extended or adjusted under 35 U.S.C. 154(b) by 117 days.

(21) Appl. No.: 13/867,174

(22) Filed: Apr. 22, 2013

(65) Prior Publication Data

US 2013/0238004 A1  Sep. 12, 2013

Related U.S. Application Data

(63) Continuation of application No. 12/593,461, filed as application No. PCT/GB2006/000697 on Feb. 28, 2006, now abandoned.

(30) Foreign Application Priority Data

Mar. 3, 2005 (GB) .................... 0504321.1

(51) Int. Cl.
*A61B 17/32* (2006.01)
*A61B 17/00* (2006.01)

(52) U.S. Cl.
CPC ... *A61B 17/32002* (2013.01); *A61B 17/320068* (2013.01); *A61B 17/320092* (2013.01); *A61B 2017/00526* (2013.01); *A61B 2017/320072* (2013.01)

(58) Field of Classification Search
CPC ............... A61B 17/320068; A61B 17/320092; A61B 17/32002; A61B 2017/320072; A61B 2017/00526

USPC .......... 606/169, 167, 170; 604/22; 601/2, 3, 4
See application file for complete search history.

(56) References Cited

U.S. PATENT DOCUMENTS 2,528,941 A  11/1950 Bassett et al.
3,565,062 A  2/1971 Kuris
(Continued)

FOREIGN PATENT DOCUMENTS

EP  0619993 A1  10/1994
EP  0646435 A1  4/1995
(Continued)

OTHER PUBLICATIONS

PCT Written Opinion of the International Search Authority for PCT/GB2007/001968 filed May 25, 2007, European Patent Office.
(Continued)

*Primary Examiner* — Ryan J Severson
*Assistant Examiner* — Anh Dang
(74) *Attorney, Agent, or Firm* — Heslin Rothenberg Farley & Mesiti P.C.

(57) ABSTRACT

The ultrasonic surgical tool has an elongate waveguide operatively connected or connectable at a proximal end to a source of ultrasonic vibrations. At a distal end, an operative element comprises a radially-extending ridge defined between a substantially parallel pair of grooves extending longitudinally of the waveguide. The operative element is curved in a plane transverse to that of the ridge. This arrangement is ergonomically superior and allows a surgeon to work for longer and with improved control. It also allows a clear visualization of the operative elements of the tool and the target tissue.

7 Claims, 1 Drawing Sheet

(56) References Cited

U.S. PATENT DOCUMENTS

| | | | |
|---|---|---|---|
| 3,657,056 | A | 4/1972 | Garvey et al. |
| 3,792,701 | A | 2/1974 | Kloz et al. |
| 3,861,391 | A | 1/1975 | Antonevich et al. |
| 4,144,646 | A | 3/1979 | Takemoto et al. |
| 4,188,952 | A | 2/1980 | Loschilov et al. |
| 4,248,232 | A | 2/1981 | Engelbrecht et al. |
| 4,832,683 | A | 5/1989 | Idemoto et al. |
| 5,019,083 | A | 5/1991 | Klapper et al. |
| 5,151,099 | A | 9/1992 | Young et al. |
| 5,167,619 | A | 12/1992 | Wuchinich |
| 5,322,055 | A | 6/1994 | Davison et al. |
| 5,324,297 | A | 6/1994 | Hood et al. |
| 5,324,299 | A | 6/1994 | Davison et al. |
| 5,330,481 | A | 7/1994 | Hood et al. |
| 5,413,107 | A | 5/1995 | Oakley et al. |
| 5,520,678 | A | 5/1996 | Heckele et al. |
| 5,549,544 | A | 8/1996 | Young et al. |
| 5,656,015 | A | 8/1997 | Young |
| 5,695,510 | A | 12/1997 | Hood |
| 5,749,877 | A | 5/1998 | Young |
| 5,873,873 | A | 2/1999 | Smith et al. |
| 5,885,301 | A | 3/1999 | Young |
| 5,935,143 | A | 8/1999 | Hood et al. |
| 6,004,335 | A | 12/1999 | Vaitekunas et al. |
| 6,056,735 | A | 5/2000 | Okada et al. |
| 6,129,735 | A | 10/2000 | Okada et al. |
| 6,283,981 | B1 | 9/2001 | Beaupre |
| 6,425,906 | B1 | 7/2002 | Young et al. |
| 6,971,994 | B1 | 12/2005 | Young et al. |
| 6,976,969 | B2 | 12/2005 | Messerly |
| 8,025,630 | B2 * | 9/2011 | Murakami et al. ............ 601/2 |
| 2002/0099400 | A1 | 7/2002 | Wolf et al. |
| 2002/0128674 | A1 | 9/2002 | Beaupre |
| 2002/0143355 | A1 | 10/2002 | Messerly |
| 2004/0044356 | A1 | 3/2004 | Young et al. |
| 2005/0021065 | A1 | 1/2005 | Yamada et al. |
| 2005/0049546 | A1 * | 3/2005 | Messerly et al. ............ 604/22 |
| 2005/0177184 | A1 | 8/2005 | Easley |

FOREIGN PATENT DOCUMENTS

| | | |
|---|---|---|
| EP | 0970659 A1 | 1/2000 |
| EP | 0970660 A1 | 1/2000 |
| EP | 1138264 A1 | 10/2001 |
| EP | 1229515 A2 | 8/2002 |
| EP | 1625836 A1 | 2/2006 |
| EP | 1693027 A | 8/2006 |
| GB | 2333709 A | 8/1999 |
| GB | 2365775 A | 2/2002 |
| GB | 2425480 A | 11/2006 |
| SU | 1388002 A1 | 4/1988 |
| WO | 99/35982 A1 | 7/1999 |
| WO | 99/52489 A1 | 10/1999 |
| WO | 01/21079 A1 | 3/2001 |
| WO | 01/24714 A1 | 4/2001 |
| WO | 02/38057 A1 | 5/2002 |
| WO | 03/047769 A1 | 6/2003 |
| WO | 03/082132 A1 | 10/2003 |
| WO | 03/082133 A1 | 10/2003 |
| WO | 2005/084553 A1 | 9/2005 |
| WO | 2006/008502 A2 | 1/2006 |
| WO | 2006/059120 A1 | 6/2006 |
| WO | 2006/092576 A1 | 9/2006 |
| WO | 2007/138295 A1 | 12/2007 |
| WO | 2008/065323 A1 | 6/2008 |

OTHER PUBLICATIONS

PCT International Search Report for PCT/GB2007001968 filed May 25, 2007, dated Sep. 12, 2007.
PCT International Search Report for PCT/GB2007/003560 filed Sep. 18, 2007, dated Jan. 3, 2008.
GB Search Report for GB 0718476.5 dated Nov. 29, 2007.
PCT International Preliminary Report on Patentability for PCT/GB2007/003560 filed Sep. 18, 2007, dated Mar. 24, 2009.
PCT International Preliminary Report on Patentability for PCT/GB2006/000697 filed Feb. 28, 2006, dated Sep. 11, 2007.
International Search Report for PCT/GB2006/000697 dated May 3, 2006.
GB Search Report for GB 0504321.1 dated Jun. 27, 2006.

* cited by examiner

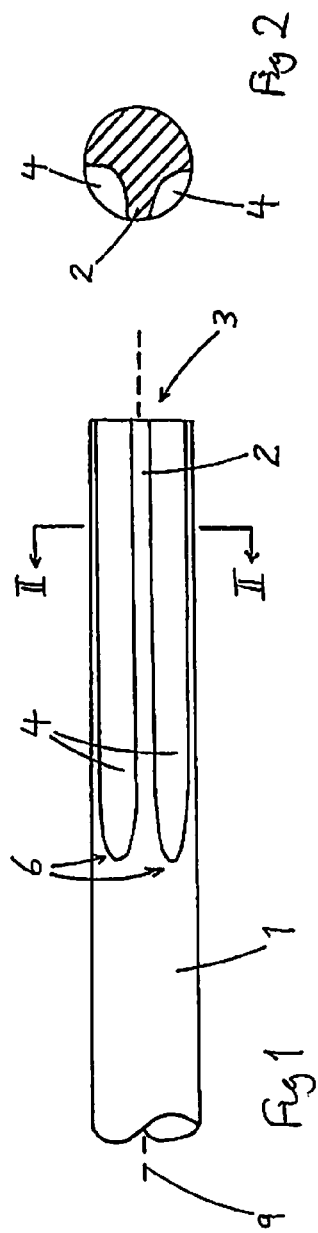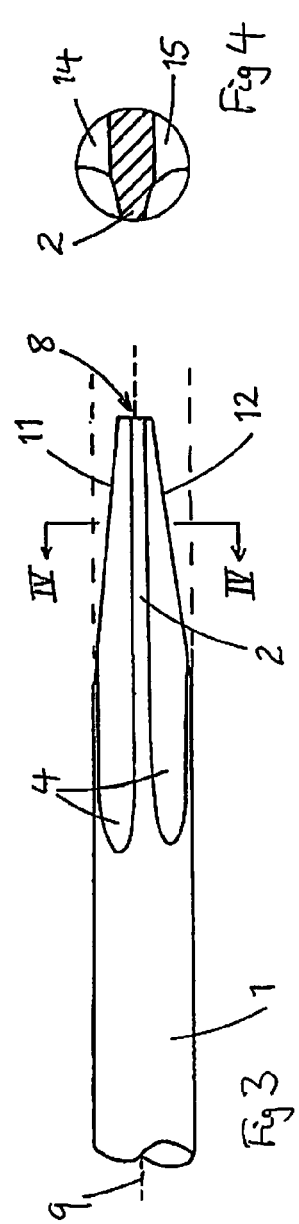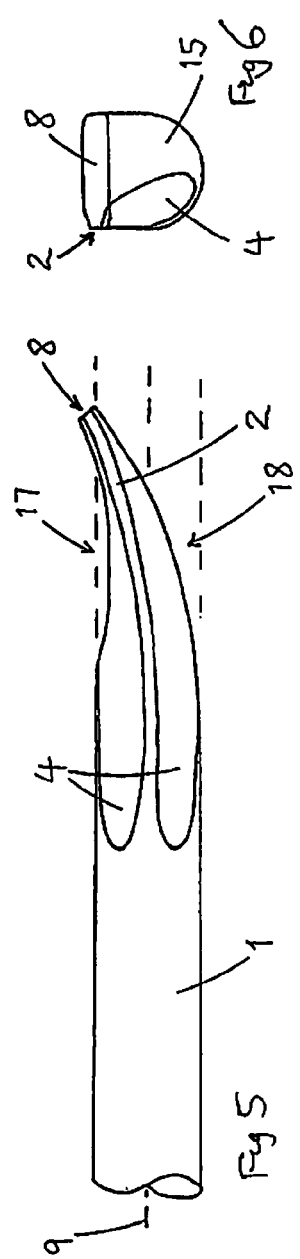

ULTRASONIC CUTTING TOOL

CROSS-REFERENCE TO RELATED APPLICATIONS

This application is a continuation of application Ser. No. 12/593,461 filed on Apr. 15, 2010, now abandoned, which claims priority to PCT International Application No. PCT/GB2006/00697 filed on Feb. 28, 2006, which was published as Publication No. WO 2006/092576 on Sep. 8, 2006, which claims priority to GB0504321.1 filed on Mar. 3, 2005.

BACKGROUND ART

The present invention relates to an ultrasonic surgical tool, such as an ultrasonic laparoscopic tool for cutting soft body tissues. More particularly, but not exclusively, it relates to such a tool having an operative tip that is profiled to improve the ergonomics of its use.

Ultrasonically-vibrated cutting tools have proven of major benefit for surgery, particularly laparoscopic surgery (so-called "keyhole" surgery). An elongate, narrow surgical tool, usually together with a fibre-optic endoscope viewing system, is introduced through a small incision into a patient's body and directed to an exact region of tissue requiring surgery. In more complex procedures, further tools may be introduced, by way of further incisions, then directed to the same site, although this is avoided wherever possible. In any case, a basic aim of laparoscopic surgery is to minimise the size and number of incisions (or "ports") made into the patient's body.

The constraints inherent in working with long, narrow tools in a confined space under remote viewing (for example on a monitor screen) mean that ergonomic design of laparoscopic tools is of paramount importance.

Ultrasonically-vibratable tools bring significant benefits in such minimally invasive procedures, as they may be selectably energised so as to cut only target tissues, and they may easily be adapted to cauterise tissue as they cut. Thus, blood vessels may be both severed and sealed in one operation, for example, significantly reducing bleeding. Such haemostatic cutting is of particular benefit in laparoscopic surgery, where visibility is at a premium.

Torsional-mode ultrasonic vibrations have proven particularly effective, since they may be transmitted efficiently and precisely into selected target tissues with minimal extraneous leakage of ultrasonic energy, whereas the alternative longitudinal-mode (or compression-wave) ultrasonic vibrations may lead to undesirable propagation of energy longitudinally out of a distal end of a tool into adjacent (non-target) tissues.

A conventional ultrasonically-vibratable laparoscopic tool, whether torsional-mode or longitundinal-mode, comprises an operative element or elements extending longitudinally from a distal end of an elongate waveguide. A surgeon manipulates the tool by grasping a handgrip mounted adjacent the proximal end of the waveguide, which extends through a restricted port into a patient's body. The operative elements are thus ideally positioned to be employed on tissues substantially directly in line with the axis of the waveguide. However, to work on tissue located to one side of the axis of the waveguide, the surgeon must partially withdraw and realign the tool, constrained by the dimensions of the port and at all times manipulating the tool by its proximal end. The continual repositioning required in a complex procedure may rapidly lead to fatigue on the part of the surgeon. There is hence a need for an ergonomically superior tool that allows the surgeon to work for longer and with improved control.

As mentioned above, another important ergonomic issue in laparoscopy is clear visualisation of the operative elements of the tool and the target tissue. An endoscope viewing system is inserted through a further incision, but this may arrive at the target tissue at such an acute angle to the tool that three dimensional visualisation is difficult.

It is hence an object of the present invention to provide an ultrasonic cutting and/or coagulating tool that obviates the above disadvantages and allows a user to conduct laparoscopic surgery more conveniently and with improved control.

SUMMARY OF THE INVENTION

According to the present invention, there is provided an ultrasonic surgical tool comprising an elongate waveguide operatively connected or connectable at a proximal end to a source of ultrasonic vibrations and provided adjacent a generally-cylindrical distal end with an operative element comprising a radially-extending ridge defined between a substantially parallel pair of grooves extending longitudinally of the waveguide from a distal end thereof, said operative element being curved in a plane transverse to that of the ridge.

The operative element may be curved in a plane substantially perpendicular to that of the ridge.

Preferably, the operative element is tapered towards its distal end.

Advantageously, the operative element comprises two convergent faces extending transversely to the plane of curvature of the operative element.

A first said convergent face may thus be concavely curved and a second said convergent face convexly curved.

The operative element may comprise a substantially blunt distal tip.

Preferably, the ridge means extends in a plane generally bisecting those of the convergent faces.

Advantageously, the first, concave convergent face converges towards the plane of the ridge more gradually than does the second, convex convergent face.

The operative element thus comprises more material between the plane of the ridge and the concave convergent face than between the plane of the ridge and the convex convergent face.

Preferably, the ridge forms a cutting edge of the operative element.

Advantageously, the operative element comprises a jaw member controllably pivotably moveable into and out of engagement with the ridge.

The jaw member may be curved correspondingly with the ridge.

The jaw member may comprise a contact surface so formed as to be cooperable with the ridge.

In a preferred embodiment, the tool comprises a source of torsional mode ultrasonic vibrations.

The tool preferably comprises means whereby the operative element may be selectably rotated about a longitudinal axis of the waveguide so as to be presented to a desired element of tissue on which to act.

An embodiment of the present invention will now be more particularly described, by way of example and with reference to the accompanying drawings, in which:

FIG. 1 is a plan view from above of a tip of an ultrasonic tool embodying the present invention, at a first stage of its production;

FIG. 2 is a cross-sectional view of the tip of the tool shown in FIG. 1, taken along the line II-II;

FIG. 3 is a plan view from above of the tip of the tool shown in FIG. 1, at a second stage of its production;

FIG. 4 is a cross-sectional view of the tip of the tool shown in FIG. 3, taken along the line IV-IV;

FIG. 5 is a plan view from above of the tip of the tool shown in FIG. 1, at a last stage of its production; and FIG. 6 is a distal end elevation of the tip of the tool shown in FIG. 5.

Referring now to the Figures, and to FIGS. 1 and 2 in particular, a narrow elongate cylindrical waveguide 1 comprises a hard, corrosion resistant material, ideally titanium or an alloy thereof. FIG. 1 shows the waveguide 1 after a first stage of the production of a tool tip thereon. Two parallel grooves 4 extend longitudinally of the waveguide 1 from its distal end 3, defining between them an upstanding rib or ridge 2. The grooves 4 blend into the cylindrical surface of the waveguide 1 at their proximal ends 6, and deepen towards the distal end 3 of the waveguide 1. The upstanding rib 2 extends in parallel to a longitudinal axis 9 of the waveguide 1. (For the purposes of this description, the rib 2 will be taken as a top of the waveguide 1, and a plane extending through the rib 2 and the longitudinal axis 9 is thus considered to be a vertical plane.)

In a second stage of the production of the tip of the tool, the result of which is shown in FIGS. 3 and 4, the distal end 3 of the waveguide 1 is tapered by machining a pair of vertically extending flats 11, 12 into it. The flats 11, 12 converge towards the distal end 3, but if prolonged would only meet beyond it. They thus leave a narrow, flat distal tip 8, which is wider than the rib 2.

The flats 11, 12 begin each level with the other at their proximal ends, but extend at slightly different angles, a first flat 11 extending at a lesser angle to the rib 2 than a second flat 12. As a result, the tip 8 is asymmetric, slightly more material remaining to a side of the rib 2 adjacent the first flat 11 than to a side of the rib 2 adjacent the second flat 12.

In cross-section (FIG. 4), the waveguide 1 now begins to take the form of a blade with a first 14 and a second 15 face formed by the respective flats 11, 12.

In the final stage of production, the result of which is shown in FIGS. 5 and 6, a distal portion of the waveguide 1 is bent round a vertically extending mandrel, so that the first face 14 adopts a concave profile 17 and the second face 15 adopts a slightly shallower convex profile 18. As a result, the rib 2 is also curved, and the tip 8 is deflected outwardly, away from the axis 9 of the waveguide 1, until it extends beyond a cylindrical volume extending distally from a distal extremity of the waveguide 1.

The waveguide tip shown in FIG. 5 forms the cutting blade of an ultrasonically-vibratable laparoscopic surgical tool. The waveguide 1 is connected at its proximal end to a generator of torsional-mode ultrasonic vibrations and to a handgrip graspable by a surgeon, and is provided along almost its entire length with a sleeve to isolate tissue through which it passes from ultrasonic vibrations transmitted along the waveguide 1. The rib 2, and in particular regions of the grooves 4 immediately flanking the rib 2 will best transmit ultrasonic energy into tissue contacted by the waveguide 1.

The tapering of the waveguide 1 towards the distal tip 8 produces a tool with a much finer dissecting profile than would an equivalent untapered distal end 3 of a waveguide 1. The tapering also facilitates the step of bending the waveguide 1 around the mandrel. One further benefit is that the taper towards the distal tip 8, which is now significantly displaced from the longitudinal/torsional axis 9, reduces the moment of inertia of the tip 8. This reduces any tendency to generate unwanted unbalanced transverse vibrational modes adjacent the distal tip 8. As can be seen from FIG. 6, the distal tip 8 is pared down to a minimum consistent with supporting the rib 2. Were it much narrower, it might risk physically cutting into tissue as it is introduced into the body, whereas an ideal laparoscopic tool is functionally blunt until the moment that it is activated.

The shape of the tool shown allows it to be used as a very delicate probe or dissector until a distal portion of the rib 2 is brought into contact with the tissue to be treated, and is ultrasonically vibrated, at which point it becomes a very precise cutting/coagulating tool.

The shape is of particular advantage over existing tools when the waveguide 1 is made rotatable about the axis 9, for example using an arrangement such as that disclosed in our copending UK Patent Application No. 0500937.8. This allows the distal tip 8 to be applied to tissue all around the end 3 of the waveguide 1, by simply "dialling" a desired angular alignment of the distal tip 8, then for example sliding it under an adjacent vessel, and ultrasonically activating it to make the required cut.

A conventional operative tip of an ultrasonic laparoscopic tool extends longitudinally from the distal end of the waveguide, and so can only easily act on tissue directly in front of the tool. The surgeon would then have to realign the entire elongate tool, constrained by the size of the incision through which it passes, to work on selected tissue that is not directly in the initial path of the tool. The form of tip 8 shown gives the surgeon a far greater radius of action without needing to reposition the whole tool, a significant ergonomic improvement.

The distal tip 8 profile shown is also usable with a controllably pivotable non-vibrated jaw mechanism, of the form used in conventional linearly-arranged tools. This comprises a jaw member with a curvature corresponding with that of the rib 2, which would be brought down into contact with an upper surface of the rib 2 to trap tissue to be cut and coagulated therebetween. Optionally, a contact surface of the jaw member would be so profiled as to cooperate with the cross-sectional profile of the rib 2 and at least the flanking regions of the grooves 4 when it closes.

The distal tip 8 profile shown is of particular benefit in procedures such as a cholecystectomy on the gall bladder, in which curved cutting planes are preferred over simple flat cuts.

Clearly, with the distal tip 8 displaced outwardly from the waveguide 1, it is also easier to see in the field of view of a conventionally positioned endoscope viewer. This improved visibility aids the surgeon in carrying out swift and accurate procedures.

The invention claimed is:

1. An ultrasonic surgical tool comprising:
an elongate waveguide,
a source of torsional mode ultrasonic vibrations operatively connected or connectable to a proximal end of said waveguide,
an operative element having a proximal end adjacent a generally cylindrical distal end of said waveguide and comprising a radially-extending ridge defined between a substantially parallel pair of grooves extending longitudinally of the waveguide and deepening from a distal end of the waveguide to a distal end of the operative element, a first of said substantially parallel pair of grooves being longer than a second of said substantially parallel pair of grooves in a plane parallel to said ridge, said operative element being curved in a plane transverse to a plane of the ridge, said operative element converging in a longitudinal direction from the proximal end to the distal end of the operative element, wherein, when the tool is operated in torsional vibrational mode, the ridge and regions of the grooves flanking the ridge are configured to transmit ultrasonic energy into a tissue, and wherein the operative element further comprises first and second vertically extending flats, wherein said first and second flats converge towards the distal end of the operative element and begin each level with the other at their proximal ends, wherein the first flat extends at a lesser angle to the ridge than the second flat, and wherein a tip formed by the first and second flats is asymmetric about said ridge, said tip having more material remaining to a side of the ridge adjacent to the first flat than to a side of the ridge adjacent to the second flat.

2. A tool as claimed in claim 1, wherein the operative element is curved in a plane substantially perpendicular to the plane of the ridge.

3. A tool as claimed in claim 1, wherein each groove of the substantially parallel pair of grooves tapers in a longitudinal direction.

4. A tool as claimed in claim 1, wherein the operative element has a substantially blunt distal tip.

5. A tool as claimed in claim 1, wherein the operative element comprises two convergent faces extending transversely to the plane of curvature of the operative element, with a first of said convergent faces being concavely curved and a second of said convergent faces being convexly curved.

6. A tool as claimed in claim 5, wherein the ridge extends in a plane generally bisecting the first convergent face from the second convergent face, and the first concave convergent face converges towards the plane of the ridge more gradually than does the second convex convergent face.

7. A tool as claimed in claim 1, wherein the operative element is adapted to be selectively rotated about a longitudinal axis of the waveguide so that the operative element is presented to a desired element of tissue on which to act.

* * * * *